United States Patent [19]

Tsaklakidis et al.

[11] Patent Number: 4,999,361

[45] Date of Patent: Mar. 12, 1991

[54] TRISUBSTITUTED AMINES, PHARMACOLOGICALLY ACCEPTABLE SALTS THEREOF AND PHARMACEUTICAL COMPOSITIONS CONTAINING THEM

[75] Inventors: Christos Tsaklakidis, Weinheim; Herbert Leinert, Heppenheim; Peter Freund, Ketsch, all of Fed. Rep. of Germany

[73] Assignee: Boehringer Mannheim GmbH, Mannheim, Fed. Rep. of Germany

[21] Appl. No.: 315,769

[22] Filed: Feb. 27, 1989

[30] Foreign Application Priority Data

Feb. 27, 1988 [DE] Fed. Rep. of Germany ....... 3806321

[51] Int. Cl.⁵ ..................... A61K 31/40; A61K 31/44; C07D 207/06
[52] U.S. Cl. .................... 514/333; 514/338; 514/343; 514/422; 514/428; 546/256; 546/281; 548/517; 548/527; 548/526; 548/569; 548/570; 548/573; 548/574; 548/575
[58] Field of Search ............... 546/281, 194, 322, 326, 546/256; 544/131; 514/237.2, 318, 343, 354, 356, 333, 338, 422, 428; 548/517, 526, 527, 569, 573, 574, 575

[56] References Cited

FOREIGN PATENT DOCUMENTS 2223006 11/1974 France .............................. 514/237.2
1050177 12/1966 United Kingdom ................ 546/322

Primary Examiner—Joseph Paul Brust
Assistant Examiner—Jacqueline Haley
Attorney, Agent, or Firm—Armstrong, Nikaido, Marmelstein, Kubovcik & Murray

[57] ABSTRACT

The present invention provides compounds of the general formula

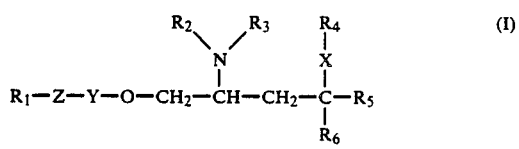

wherein $R_1$ is a hydrogen atom, a straight-chained or branched $C_1$–$C_{12}$-alkyl radical, a $C_3$–$C_7$-cycloalkyl radical, a straight-chained or branched $C_2$–$C_{12}$-alkenyl radical or an unsubstituted or substituted $C_3$–$C_7$-mono- or bicycloalkenyl radical, an unsubstituted or singly or multiple substituted monocyclic aromatic or heteroaromatic radical, $R_2$ and $R_3$, which can be the same or different, are straight-chained, branched, saturated or unsaturated $C_1$–$C_6$-aliphatic radicals or, together with the nitrogen atom to which they are attached, form a saturated or unsaturated ring which can contain further heteroatoms and can optionally be substituted by a lower alkyl radical, a lower alkoxy radical or an oxygen atom, $R_4$ is an unsubstituted or singly or multiple substituted monocyclic aromatic radical, an unsubstituted or substituted five- or six-membered heteroaromatic ring, $R_5$ is a hydrogen atom, a cyano radical, a —CO—OR$_7$ radical, an unsubstituted or a singly or multiple substituted monocyclic aromatic radical or an unsubstituted or substituted five- or six-membered ring, $R_6$ is a hydrogen atom, a cyano group or a —CO—OR$_7$,

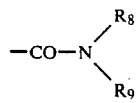

or —CH$_2$—O—R$_{10}$ radical, $R_7$ is a hydrogen atom, a $C_1$–$C_{12}$-alkyl radical or an N-dialkylamino-$C_1$–$C_6$-alkyl radical, $R_8$ and $R_9$, which can be the same or different, are hydrogen atoms or straight-chained, branched, saturated or unsaturated aliphatic $C_1$–$C_{12}$-aliphatic radicals or, together with the nitrogen atom to which they are attached, form a saturated or unsaturated ring with 2 to 6 carbon atoms, $R_{10}$ is a hydrogen atom, a straight-chained or branched $C_1$–$C_6$-alkyl or $C_2$–$C_6$-alkenyl radical, an aralkyl radical or an acyl radical, X is a valency bond or a methylene radical, Y is a valency bond or a straight-chained, branched, saturated or unsaturated hydrocarbon radical containing up to 6 carbon atoms and Z is a valency bond, or oxygen atom or a carbonyl group; as well as the pharmacologically acceptable salts and optical isomers thereof.

The present invention also provides processes for the preparation of these compounds, as well as pharmaceutical compositions containing them for the treatment of heart and circulatory diseases.

16 Claims, No Drawings

TRISUBSTITUTED AMINES, PHARMACOLOGICALLY ACCEPTABLE SALTS THEREOF AND PHARMACEUTICAL COMPOSITIONS CONTAINING THEM

The present invention is concerned with new trisubstituted amines, the pharmacologically acceptable salts thereof, processes for the preparation thereof and pharmaceutical compositions containing them.

The new amino compounds according to the present invention have the general formula:

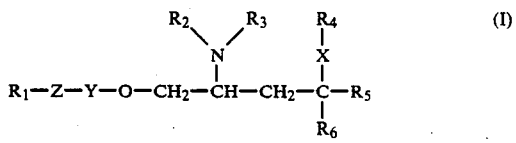

wherein $R_1$ is a hydrogen atom, a straight-chained or branched $C_1-C_{12}$-alkyl radical, a $C_3-C_7$-cycloalkyl radical, a straight-chained or branched $C_2-C_{12}$-alkenyl radical or an unsubstituted or substituted $C_3-C_7$-mono- or bicycloalkenyl radical, an unsubstituted or singly or multiple substituted monocyclic aromatic or heteroaromatic radical, $R_2$ and $R_3$, which can be the same or different, are straight-chained, branched, saturated or unsaturated $C_1-C_6$-aliphatic radicals or, together with the nitrogen atom to which they are attached, form a saturated or unsaturated ring which can contain further heteroatoms and can optionally be substituted by a lower alkyl radical, a lower alkoxy radical or an oxygen atom, $R_4$ is an unsubstituted or singly or multiple substituted monocyclic aromatic radical, an unsubstituted or substituted five- or six-membered heteroaromatic ring, $R_5$ is a hydrogen atom, a cyano radical, a $-CO-OR_7$ radical, an unsubstituted or a singly or multiple substituted monocylic aromatic radical or an unsubstituted or substituted five- or six-membered ring, $R_6$ is a hydrogen atom, a cyano group or a $-CO-OR_7$,

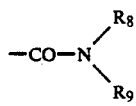

or $-CH_2-O-R_{10}$ radical, $R_7$ is a hydrogen atom, a $C_1-C_{12}$-alkyl radical or an N-dialkylamino-$C_1-C_6$-alkyl radical, $R_8$ and $R_9$, which can be the same or different, are hydrogen atoms or straight-chained, branched, saturated or unsaturated aliphatic $C_1-C_{12}$-aliphatic radicals or, together with the nitrogen atom to which they are attached, form a saturated or unsaturated ring with 2 to 6 carbon atoms, $R_{10}$ is a hydrogen atom, a straight-chained or branched $C_1-C_6$-alkyl or $C_2-C_6$-alkenyl radical, an aralkyl radical or an acyl radical, X is a valency bond or a methylene radical, Y is a valency bond or a straight-chained, branched, saturated or unsaturated hydrocarbon radical containing up to 6 carbon atoms and Z is a valency bond, or oxygen atom or a carbonyl group; as well as the pharmacologically acceptable salts and optical isomers thereof.

The $C_1-C_{12}$-alkyl radical $R_1$ is preferably a methyl, ethyl, propyl, isopropyl, isobutyl, isoamyl, isohexyl, n-hexyl, n-octyl or n-dodecyl radical, especially an isobutyl, isoamyl or isohexyl radical. The $C_3-C_7$-cycloalkyl radical is usually a cyclopentyl or cyclohexyl radical. $C_2-C_{12}$-alkenyl radicals are preferably allyl, methallyl, isopentenyl, prenyl, 1,1-dimethyl-2-propenyl or geranyl radicals. The $C_3-C_7$-mono- or bicycloalkenyl radical is usually a cyclopentenyl, cyclohexenyl or myrtenyl radical.

$R_2$ and $R_3$ are preferably methyl, ethyl, propyl, allyl or methallyl radicals. Rings which $R_2$ and $R_3$ form, together with the nitrogen atom to which they are attached, are preferably the pyrrolidine or the piperidine rings and especially the pyrrolidine ring. The heteroatoms which the rings can contain are nitrogen, sulphur and oxygen. Hereunder are to be understood rings such as piperazine, morpholine and thiomorpholine. Substituents of the above-mentioned rings are, in particular, $C_1-C_3$-alkyl and $C_1-C_3$-alkoxy radicals, for example methyl, ethyl, propyl, methoxy, ethoxy and propoxy radicals. As a rule, the oxygen atom, together with the carbon atom to which it is attached, represents a carbonyl group. Corresponding rings include, for example the pyrrolidone and piperidone rings.

The unsubstituted or substituted aromatic radical of the radicals $R_1$, $R_4$ and $R_5$ signifies a phenyl radical or a phenyl radical substituted one or more times, the especially preferred substituents being $C_1-C_6$-alkyl, $C_2-C_6$-alkenyl, $C_1-C_6$-alkoxy, $C_2-C_6$-alkenyloxy, hydroxyalkyl, $C_1-C_6$-alkylendioxy, hydroxyalkoxy, alkoxyalkoxy, alkylamino, dialkylamino, alkoxycarbonylalkoxy, phenylthio, alkylsulphinyl, alkylsulphonyl, alkylsulphonyloxycarboxy, alkoxycarbonyl, aminocarbonyl, mono- and dialkylaminocarbonyl, haloalkyl and cyano radicals, as well as halogen atoms, such as chlorine, bromine or fluorine atoms.

Heteroaromatic radicals of the substituents $R_1$, $R_4$ and $R_5$ are preferably pyridyl, pyrimidinyl, pyrazinyl, thienyl, oxazolyl, pyrazolyl, imidazolyl, tetrazolyl, thiazolyl and isoxazolyl radicals and especially pyridyl, furanyl and thienyl radicals.

The $C_1-C_{12}$-alkyl radical of $R_7$, $R_8$ and $R_9$ preferably signifies a methyl, ethyl, propyl, isopropyl, isobutyl, isoamyl, isohexyl, n-hexyl, n-octyl or ndodecyl radical. The N-dialkylamino-($C_1-C_6$)-alkyl radical usually means a methyl, ethyl, propyl or hexyl radical substituted by a dimethylamino or diethylamino moiety and is preferably a dimethylaminoethyl radical.

Rings which $R_8$ and $R_9$ can form, together with the nitrogen atom to which they are attached, are preferably pyrrolidine or piperidine rings.

The $C_1-C_6$-alkyl radical of the substituent $R_{10}$ is preferably a methyl, propyl or isobutyl radical. The $C_2-C_6$-alkenyl radical is preferably an allyl, methallyl or isobutenyl radical. As a rule, the aralkyl radical is a benzyl or picolyl radical. Acyl radicals are preferably residues of aliphatic $C_1-C_6$-carboxylic acids, for example formyl, acetyl or pivaloyl, or of arylcarboxylic acids, for example benzoyl.

Preferred compounds of general formula (I) according to the present invention are those in which $R_1$ is an isobutyl, methallyl, isopentenyl, prenyl, 1,1-dimethyl-2-propenyl, furyl, thienyl, pyridyl or phenyl radical or a phenyl radical which is substituted by methyl, methoxy or halogen, $R_2$ and $R_3$ are both ethyl radicals or, together with the nitrogen atom to which they are attached, a pyrrolidine, piperidine or morpholine ring, $R_4$ is a furyl, thienyl, pyridyl or phenyl radical or a phenyl radical substituted by methyl, methoxy or halogen, $R_5$ a hydrogen atom, a cyano group or an ethoxycarbonyl, furyl, thienyl, pyridyl or phenyl radical or a phenyl radical substituted by methyl, methylenedioxy, methoxy or halogen, $R_6$ is a hydrogen atom, a cyano group or a methoxycarbonyl, ethoxycarbonyl, n-propoxycarbonyl, isopropoxycarbonyl, aminocarbonyl, diethylaminocarbonyl, dimethylaminoethoxycarbonyl, piperidinocarboxyl or hydroxylmethyl radical, X is a valency bond or a methylene radical, Y is a valency bond or a methylene or ethylene radical and Z is a valency bond, an oxygen atom or a carbonyl group; as well as the pharmacologically acceptable salts and optical isomers thereof.

The compounds of general formula (I) according to the present invention can be prepared in known manner by (a) reacting a compound of the general formula:

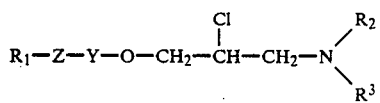
(II)

wherein Y, Z, $R_1$, $R_2$ and $R_3$ have the above-given meanings, with a compound of the general formula:

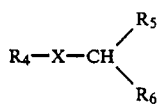
(III)

in which X, $R_4$, $R_5$ and $R_6$ have the above-given meanings, or (b) reacting a compound of the general formula:

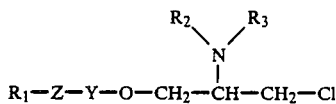
(IV)

in which Y, Z, $R_1$, $R_2$ and $R_3$ have the above-given meanings, with a compound of general formula (III), and subsequently, if desired, converting the compound obtained into another compound of general formula (I).

The reaction of a compound of general formula (II) or (IV) with a compound of general formula (III) to give a compound of general formula (I) according to the present invention takes place in known manner in an inert solvent, for example toluene, xylene, dimethylformamide or tetrahydrofuran, at a temperature of from 20° C. to the reflux temperature of the solvent in the presence of an alkaline condensation agent, for example sodium hydride or lithium diisopropylamide.

The compounds of general formula (II) can be prepared by reacting a compound of the general formula:

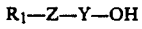
$R_1$—Z—Y—OH (V)

in which Y, Z and $R_1$ have the above-given meanings, with epichlorohydrin in the presence of an aqueous solution of sodium hydroxide and of a phase transfer catalyst, for example tetrabutylammonium bromide, reacting the compound thus obtained of the general formula:

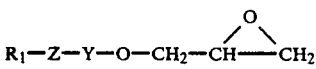
(VI)

in which $R_1$, Y and Z have the above-given meanings, with an amine of the general formula:

$R_2$—NH—$R_3$ (VII)

in which $R_2$ and $R_3$ have the above-given meanings, to give an alcohol of the general formula:

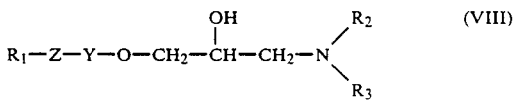
(VIII)

in which $R_1$, $R_2$ and $R_3$ have the above-given meanings, which is reacted with thionyl chloride in an inert solvent.

The compounds of general formula (IV) can be prepared by reducing a compound of the general formula:

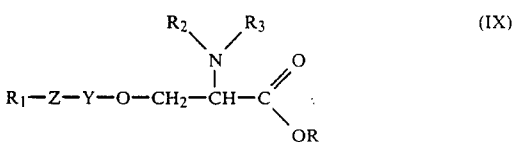
(IX)

in which Y, Z, $R_1$, $R_2$ and $R_3$ have the above-given meanings and R is an alkyl radical, with a complex hydride, for example lithium aluminium hydride, in an inert solvent in known manner to give a compound of the general formula:

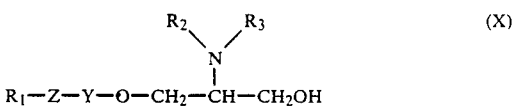
(X)

in which Y, Z, $R_1$, $R_2$ and $R_3$ have the above-given meanings, and chlorinating this with thionyl chloride in an inert solvent.

The subsequent conversion of compounds of general formula (I) into other compounds applies, for example, to the conversion of the substituent $R_6$. For this purpose, the ester usually used is saponified to the free carboxylic acid or reduced to the corresponding alcohol.

The starting compounds of general formula (IX) can be prepared by the process described in Federal Republic of Germany Patent Specification No. 28 02 864.

The compounds of general formula (I) according to the present invention contain one or two asymmetric carbon atoms. Therefore, the present invention also includes the diastereomers, racemates and optically-active forms of the compounds of general formula (I) according to the present invention. If diastereomers are obtained in the case of the synthesis of the compounds according to the present invention, then these can be separated into the corresponding racemates by column chromatography.

The optically-active compounds can be prepared from the racemic mixtures thereof by known methods by way of diastereomeric salts. For the resolution, there can be used, for example, tartaric acid, malic acid, camphoric acid, camphor-sulphonic acid or dibenzoyltartaric acid.

For the conversion of the compounds of general formula (I) into their pharmacologically acceptable salts, these are reacted, preferably in an organic solvent, with an equivalent amount of an inorganic or organic acid, for example, hydrochloric acid, hydrobromic acid, phosphoric acid, sulphuric acid, acetic acid, salicylic acid, citric acid, benzoic acid, naphthoic acid, o-acetoxybenzoic acid, adipic acid, maleic acid or oxalic acid.

The compounds of general formula (I) according to the present invention possess valuable pharmacological properties. They are especially characterised by a blood vessel-relaxing action and can, therefore, be used for the therapy of heart-circulatory diseases.

The compounds of general formula (I) according to the present invention and the salts thereof can be administered enterally or parenterally in liquid or solid form. As injection medium it is preferred to use water which contains the additives usual in the case of injection solutions, for example stabilising agents, solubilising agents and/or buffers. Such additives include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, the state of health and the weight of the recipient, the extent of the disease, the nature of possibly simultaneously carried out further treatment, the frequency of the treatment and the nature of the desired action. An appropriate daily dosage of the active compound is from 0.01 to 50 mg./kg. of body weight, preferably 1 to 40 mg./kg. of body weight. The active compound can be administered to patients in a suitable amount, generally in an amount of 50 to 1000 mg per dose. The patient will normally be administered from 1 to 3 doses daily.

Besides the compounds described in the following Examples, the following compounds are especially preferred within the scope of the present invention. In Table 1 of the description of the in vitro test results that follows the Examples, compounds 2, 66, 70, 71 and 72 of the following table on pages 13–24 are identified as BV 2, BV 66, BV 70, BV 71 and BV 72, respectively (BV = bevorzugte Verbindung).

In the compounds of the present invention, the various radicals, when substituted, typically have one, two or three substituents, preferably one, substituent.

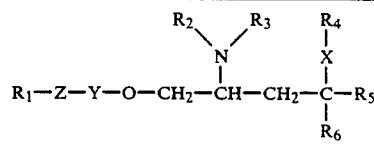

$$R_1-Z-Y-O-CH_2-\underset{\underset{N}{|}}{CH}-CH_2-\underset{\underset{R_6}{|}}{\overset{\overset{X}{|}}{C}}-R_5$$

with $R_2, R_3$ on N and $R_4$ on X.

| Ex. No. | $R_1$ | Z | Y | $R_2, R_3$ | $R_4$ | $R_5$ | $R_6$ | X |
|---|---|---|---|---|---|---|---|---|
| 1 | $(CH_3)_2-CHCH_2-$ | — | — | cyclopentyl | phenyl | phenyl | —H | $-CH_2-$ |
| 2 | $(CH_3)_2-CHCH_2-$ | — | — | cyclopentyl | 4-methoxyphenyl | phenyl | $-C(=O)OC_2H_5$ | $-CH_2-$ |
| 3 | $(CH_3)_2-CHCH_2-$ | — | — | cyclopentyl | pyridyl | phenyl | $-C(=O)OC_2H_5$ | $-CH_2-$ |
| 4 | $(CH_3)_2-CHCH_2-$ | — | — | cyclopentyl | furyl | phenyl | $-C(=O)OC_2H_5$ | $-CH_2-$ |
| 5 | $(CH_3)_2-CHCH_2-$ | — | — | cyclopentyl | thienyl | phenyl | $-C(=O)OC_2H_5$ | $-CH_2-$ |

-continued $$R_1-Z-Y-O-CH_2-CH(NR_2R_3)-CH_2-C(R_4)(R_5)(R_6) \text{ with } X$$

| Ex. No. | $R_1$ | Z | Y | $R_2, R_3$ | $R_4$ | $R_5$ | $R_6$ | X |
|---|---|---|---|---|---|---|---|---|
| 6 | $(CH_3)_2-CHCH_2-$ | — | — | cyclopentyl (ring) | phenyl | phenyl | $-C(=O)NH_2$ | — |
| 7 | $(CH_3)_2-CHCH_2-$ | — | — | $C_2H_5-$ | phenyl | phenyl | $-H$ | — |
| 8 | $(CH_3)_2-CHCH_2-$ | — | — | cyclohexyl (ring) | phenyl | phenyl | $-H$ | — |
| 9 | $(CH_3)_2-CHCH_2-$ | — | — | tetrahydropyranyl (ring with O) | phenyl | phenyl | $-H$ | — |
| 10 | $(CH_3)_2-CHCH_2-$ | — | — | $C_2H_5-$ | phenyl | phenyl | $-C(=O)NH_2$ | — |
| 11 | $(CH_3)_2-CHCH_2-$ | — | — | cyclohexyl (ring) | phenyl | phenyl | $-C(=O)NH_2$ | — |
| 12 | $(CH_3)_2-CHCH_2-$ | — | — | tetrahydropyranyl (ring with O) | phenyl | phenyl | $-C(=O)NH_2$ | — |
| 13 | $(CH_3)_2-CHCH_2-$ | — | — | $C_2H_5-$ | phenyl | phenyl | $-C\equiv N$ | — |
| 14 | $(CH_3)_2-CHCH_2-$ | — | — | cyclohexyl (ring) | phenyl | phenyl | $-C\equiv N$ | — |
| 15 | $(CH_3)_2-CHCH_2-$ | — | — | tetrahydropyranyl (ring with O) | phenyl | phenyl | $-C\equiv N$ | — |

-continued $$R_1-Z-Y-O-CH_2-\overset{\overset{R_2\quad R_3}{\underset{|}{N}}}{CH}-CH_2-\overset{\overset{R_4}{\underset{|}{X}}}{\underset{R_6}{C}}-R_5$$

| Ex. No. | R₁ | Z | Y | R₂, R₃ | R₄ | R₅ | R₆ | X |
|---|---|---|---|---|---|---|---|---|
| 16 | (CH₃)₂—CHCH₂— | — | — | (pyrrolidine) | phenyl | 4-OCH₃-phenyl | —H | — |
| 17 | (CH₃)₂—CHCH₂— | — | — | (pyrrolidine) | 4-OCH₃-phenyl | 4-OCH₃-phenyl | —H | — |
| 18 | (CH₃)₂—CHCH₂— | — | — | (pyrrolidine) | 4-CH₃-phenyl | 4-CH₃-phenyl | —H | — |
| 19 | (CH₃)₂—CHCH₂— | — | — | (pyrrolidine) | 4-F-phenyl | 4-F-phenyl | —H | — |
| 20 | (CH₃)₂—CHCH₂— | — | — | (pyrrolidine) | phenyl | 4-OCH₃-phenyl | —C(=O)OC₂H₅ | — |
| 21 | (CH₃)₂—CHCH₂— | — | — | (pyrrolidine) | 4-CH₃-phenyl | 4-CH₃-phenyl | —C(=O)OC₂H₅ | — |
| 22 | (CH₃)₂—CHCH₂— | — | — | (pyrrolidine) | 4-F-phenyl | 4-F-phenyl | —C(=O)OC₂H₅ | — |
| 23 | (CH₃)₂—CHCH₂— | — | — | (pyrrolidine) | phenyl | 4-OCH₃-phenyl | —C(=O)NH₂ | — |

-continued $$R_1-Z-Y-O-CH_2-\underset{\underset{R_3}{\overset{R_2}{\underset{|}{N}}}}{\overset{}{CH}}-CH_2-\underset{\underset{R_6}{|}}{\overset{\overset{R_4}{|}}{\underset{|}{C}}}-R_5$$

| Ex. No. | R₁ | Z | Y | R₂, R₃ | R₄ | R₅ | R₆ | X |
|---|---|---|---|---|---|---|---|---|
| 24 | (CH₃)₂—CHCH₂— | — | — | pyrrolidinyl | 4-OCH₃-C₆H₄ | 4-OCH₃-C₆H₄ | —C(=O)NH₂ | — |
| 25 | (CH₃)₂—CHCH₂— | — | — | pyrrolidinyl | 4-CH₃-C₆H₄ | 4-CH₃-C₆H₄ | —C(=O)NH₂ | — |
| 26 | (CH₃)₂—CHCH₂— | — | — | pyrrolidinyl | 4-F-C₆H₄ | 4-F-C₆H₄ | —C(=O)NH₂ | — |
| 27 | (CH₃)₂—CHCH₂— | — | — | pyrrolidinyl | C₆H₅ | 4-OCH₃-C₆H₄ | —C≡N | — |
| 28 | (CH₃)₂—CHCH₂— | — | — | pyrrolidinyl | 4-CH₃-C₆H₄ | 4-CH₃-C₆H₄ | —C≡N | — |
| 29 | (CH₃)₂—CHCH₂— | — | — | pyrrolidinyl | 4-F-C₆H₄ | 4-F-C₆H₄ | —C≡N | — |
| 30 | (CH₃)₂—CHCH₂— | — | — | pyrrolidinyl | C₆H₅ | 2-furyl | —H | — |
| 31 | (CH₃)₂—CHCH₂— | — | — | pyrrolidinyl | 4-OCH₃-C₆H₄ | 4-OCH₃-C₆H₄ | —C(=O)OC₂H₅ | —CH₂— |

-continued $$R_1-Z-Y-O-CH_2-CH(NR_2R_3)-CH_2-C(R_4)(R_5)(R_6)X$$

where N has R_2, R_3 substituents and C has R_4, R_5, R_6 and X substituents.

| Ex. No. | R_1 | Z | Y | R_2, R_3 | R_4 | R_5 | R_6 | X |
|---|---|---|---|---|---|---|---|---|
| 32 | CH_2=C(CH_3)-CH_2- | — | — | pyrrolidinyl (cyclic) | phenyl | phenyl | -H | -CH_2- |
| 33 | CH_2=CH-CH(CH_3)- | — | — | pyrrolidinyl | phenyl | phenyl | -H | — |
| 34 | CH_2=C(CH_3)-CH_2- | — | — | pyrrolidinyl | phenyl | phenyl | -C(=O)NH_2 | — |
| 35 | CH_2=CH-C(CH_3)_2- | — | — | pyrrolidinyl | phenyl | phenyl | -H | -CH_2- |
| 36 | CH_2=CH-C(CH_3)_2- | — | — | pyrrolidinyl | phenyl | phenyl | -C(=O)OC_2H_5 | -CH_2- |
| 37 | CH_2=CH-C(CH_3)_2- | — | — | pyrrolidinyl | phenyl | phenyl | -H | — |
| 38 | (CH_3)_2C=CH-CH_2- | — | — | pyrrolidinyl | phenyl | phenyl | -H | -CH_2- |
| 39 | (CH_3)_2C=CH-CH_2- | — | — | pyrrolidinyl | phenyl | phenyl | -H | — |
| 40 | (CH_3)_2-CHCH_2- | — | — | pyrrolidinyl | phenyl | 2-thienyl | -H | — |
| 41 | (CH_3)_2-CHCH_2- | — | — | pyrrolidinyl | phenyl | 2-pyridyl | -H | — |

-continued $$R_1-Z-Y-O-CH_2-\underset{\underset{R_3}{\overset{\overset{R_2}{N}}{|}}}{CH}-CH_2-\underset{\underset{R_6}{|}}{\overset{\overset{R_4}{|}}{\underset{|}{C}}}-R_5$$

| Ex. No. | $R_1$ | Z | Y | $R_2, R_3$ | $R_4$ | $R_5$ | $R_6$ | X |
|---|---|---|---|---|---|---|---|---|
| 42 | $(CH_3)_2-CHCH_2-$ | — | — | cyclopentyl | 2-thienyl | 2-thienyl | —H | — |
| 43 | $(CH_3)_2-CHCH_2-$ | — | — | cyclopentyl | phenyl | 2-thienyl | $-C(=O)OC_2H_5$ | — |
| 44 | $(CH_3)_2-CHCH_2-$ | — | — | cyclopentyl | phenyl | 2-pyridyl | $-C(=O)OC_2H_5$ | — |
| 45 | $(CH_3)_2-CHCH_2-$ | — | — | cyclopentyl | phenyl | 2-thienyl | $-C(=O)NH_2$ | — |
| 46 | $(CH_3)_2-CHCH_2-$ | — | — | cyclopentyl | phenyl | 2-pyridyl | $-C(=O)NH_2$ | — |
| 47 | $(CH_3)_2-CHCH_2-$ | — | — | cyclopentyl | 2-thienyl | 2-thienyl | $-C(=O)NH_2$ | — |
| 48 | $(CH_3)_2-CHCH_2-$ | — | — | cyclopentyl | phenyl | 2-thienyl | $-C\equiv N$ | — |
| 49 | $(CH_3)_2-CHCH_2-$ | — | — | cyclopentyl | 2-thienyl | 2-thienyl | $-C\equiv N$ | — |
| 50 | $CH_2=C(CH_3)-CH_2CH_2-$ | — | — | cyclopentyl | phenyl | phenyl | —H | $-CH_2-$ |
| 51 | $CH_2=C(CH_3)-CH_2CH_2-$ | — | — | cyclopentyl | phenyl | phenyl | —H | — |
| 52 | $(CH_3)_2-CHCH_2-$ | — | — | cyclopentyl | phenyl | phenyl | $-C(=O)N(C_2H_5)_2$ | — |

-continued $$R_1-Z-Y-O-CH_2-\underset{\underset{R_6}{|}}{\overset{\overset{R_2}{|}}{\underset{|}{C}H}}-N\overset{R_3}{\underset{}{}}\,\,\,\,CH_2-\underset{\underset{R_6}{|}}{\overset{\overset{R_4}{|}}{\underset{|}{C}}}-R_5$$

| Ex. No. | $R_1$ | Z | Y | $R_2, R_3$ | $R_4$ | $R_5$ | $R_6$ | X |
|---|---|---|---|---|---|---|---|---|
| 53 | $(CH_3)_2-CHCH_2-$ | — | — | cyclopentyl | phenyl | phenyl | $-C(=O)-N(\text{piperidinyl})$ | — |
| 54 | $-H$ | — | — | cyclopentyl | phenyl | phenyl | $-C(=O)OC_2H_5$ | $-CH_2-$ |
| 55 | phenyl | $-C(=O)-$ | — | cyclopentyl | phenyl | phenyl | $-C(=O)OC_2H_5$ | $-CH_2-$ |
| 56 | phenyl | — | $-CH_2-$ | cyclopentyl | phenyl | phenyl | $-C(=O)OC_2H_5$ | $-CH_2-$ |
| 57 | phenyl | — | — | cyclopentyl | phenyl | phenyl | $-H$ | — |
| 58 | phenyl | — | $-CH_2-$ | cyclopentyl | phenyl | phenyl | $-H$ | — |
| 59 | phenyl | — | — | cyclopentyl | phenyl | phenyl | $-C(=O)NH_2$ | — |
| 60 | phenyl | — | $-CH_2-$ | cyclopentyl | phenyl | phenyl | $-C(=O)NH_2$ | — |
| 61 | phenyl | — | $-CH_2-$ | cyclopentyl | phenyl | phenyl | $-C\equiv N$ | — |
| 62 | 4-CH$_3$-phenyl | — | $-CH_2-$ | cyclopentyl | phenyl | phenyl | $-C(=O)OC_2H_5$ | — |

-continued $$R_1-Z-Y-O-CH_2-\underset{\underset{N}{|}}{CH}-CH_2-\underset{\underset{R_6}{|}}{\overset{\overset{R_4}{|}}{\underset{|}{C}}}-R_5$$
with $R_2, R_3$ on N and $X$ on C

| Ex. No. | R₁ | Z | Y | R₂, R₃ | R₄ | R₅ | R₆ | X |
|---|---|---|---|---|---|---|---|---|
| 63 | 4-methoxyphenyl | — | —CH₂— | pyrrolidinyl | phenyl | phenyl | —C(=O)OC₂H₅ | — |
| 64 | 4-chlorophenyl | — | —CH₂— | pyrrolidinyl | phenyl | phenyl | —C(=O)OC₂H₅ | — |
| 65 | phenyl | — | —(CH₂)₂— | pyrrolidinyl | phenyl | phenyl | —C(=O)OC₂H₅ | — |
| 66 | phenyl | — | —CH₂— | pyrrolidinyl | phenyl | phenyl | —C(=O)OCH₃ | — |
| 67 | phenyl | — | —CH₂— | pyrrolidinyl | phenyl | phenyl | —C(=O)O(CH₂)₂CH₃ | — |
| 68 | phenyl | — | —CH₂— | pyrrolidinyl | phenyl | phenyl | —C(=O)OCH(CH₃)₂ | — |
| 69 | phenyl | — | —CH₂— | pyrrolidinyl | phenyl | phenyl | —C(=O)O(CH₂)₂N(CH₃)₂ | — |
| 70 | phenyl | O | —(CH₂)₂— | pyrrolidinyl | phenyl | phenyl | —C(=O)OC₂H₅ | — |
| 71 | 2-furyl | — | —CH₂— | pyrrolidinyl | phenyl | phenyl | —C(=O)OC₂H₅ | — |
| 72 | 2-thienyl | — | —CH₂— | pyrrolidinyl | phenyl | phenyl | —C(=O)OC₂H₅ | — |

-continued

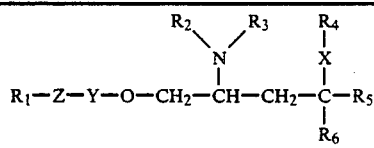

| Ex. No. | R₁ | Z | Y | R₂, R₃ | R₄ | R₅ | R₆ | X |
|---|---|---|---|---|---|---|---|---|
| 73 | 2-pyridyl | — | —CH₂— | cyclopentyl (N-N) | phenyl | phenyl | —H | — |
| 74 | (CH₃)₂—CHCH₂— | — | — | cyclopentyl (N-N) | 4-Cl-phenyl | 4-Cl-phenyl | —H | — |
| 75 | (CH₃)₂—CHCH₂— | — | — | cyclopentyl (N-N) | 4-Cl-phenyl | 4-Cl-phenyl | —C(=O)OC₂H₅ | — |
| 76 | (CH₃)₂—CHCH₂— | — | — | cyclopentyl (N-N) | 4-Cl-phenyl | 4-Cl-phenyl | —C(=O)NH₂ | — |
| 77 | (CH₃)₂—CHCH₂— | — | — | cyclopentyl (N-N) | 4-Cl-phenyl | 4-Cl-phenyl | —C≡N | — |

Ex. 2: oil, m/e 467
Ex. 20: oil, m/e 453
Ex. 27: oil, m/e 406
Ex. 56: oil, m/e 471
Ex. 58: oil, m/e 385
Ex. 61: oil, m/e 410
Ex. 62: oil, m/e 471
Ex. 63: oil, m/e 487
Ex. 64: oil, m/e 491
Ex. 65: oil, m/e 471
Ex. 66: oil, m/e 443
Ex. 67: oil, m/e 471
Ex. 68: oil, m/e 471
Ex. 69: oxalate, m.p. 125° C. ethyl acetate
Ex. 70: oil, m/e 487
Ex. 71: oil, m/e 447
Ex. 72: oil, m/e 449
Ex. 73: oil, m/e 386
Ex. 74: oil, m/e 420
Ex. 75: oil, m/e 492
Ex. 77: oil, m/e 445

For the characterisation if the compounds prepared, in many cases there are given the mass spectrometrically determined mole peaks m/e $$R_1-Z-Y-O-CH_2-CH(N(R_2)(R_3))-CH_2-C(R_4)(R_5)(X)(R_6)$$

| Ex. No. | R₁ | Z | Y | R₂, R₃ | R₄ | R₅ | R₆ | X |
|---|---|---|---|---|---|---|---|---|
| 78 | 3-chlorophenyl | — | —CH₂— | pyrrolidine (cyclic) | phenyl | phenyl | —C≡N | — |
| 79 | phenyl | — | —CH₂— | pyrrolidine | phenyl | phenyl | —CH₂—OH | — |
| 80 | 2-pyridyl | — | —CH₂— | pyrrolidine | phenyl | phenyl | —CH₂—OCH₃ | — |
| 81 | 2-pyridyl | — | —CH₂— | pyrrolidine | phenyl | phenyl | —CH₂—O—C₃H₇ | — |
| 82 | 2-pyridyl | — | —CH₂— | pyrrolidine | phenyl | phenyl | —CH₂—O—C(=O)—CH₃ | — |
| 83 | 2-pyridyl | — | —CH₂— | pyrrolidine | phenyl | phenyl | —CH₂—O—C(=O)—C(CH₃)₃ | — |
| 84 | 2-pyridyl | — | —CH₂— | pyrrolidine | phenyl | phenyl | —CH₂—O—C(=O)—phenyl | — |
| 85 | 2-pyridyl | — | —CH₂— | pyrrolidine | phenyl | phenyl | —CH₂—O—CH₂—(2-pyridyl) | — |
| 86 | 2-pyridyl | — | —CH₂— | pyrrolidine | phenyl | phenyl | —C≡N | — |
| 87 | 3-pyridyl | — | —CH₂— | pyrrolidine | phenyl | phenyl | —C≡N | — |

-continued $$R_1-Z-Y-O-CH_2-\underset{\underset{R_6}{|}}{\overset{\overset{R_2\diagdown\phantom{a}\diagup R_3}{N}}{\underset{}{|}}}CH-CH_2-\overset{\overset{R_4}{|}}{\underset{\underset{R_6}{|}}{C}}-R_5$$

| Ex. No. | R₁ | Z | Y | R₂, R₃ | R₄ | R₅ | R₆ | X |
|---|---|---|---|---|---|---|---|---|
| 88 | 4-pyridyl | — | —CH₂— | pyrrolidino | phenyl | phenyl | —C≡N | — |
| 89 | 2-chlorophenyl | — | —CH₂— | pyrrolidino | phenyl | phenyl | —C(=O)OC₂H₅ | — |
| 90 | 3-chlorophenyl | — | —CH₂— | pyrrolidino | phenyl | phenyl | —C(=O)OC₂H₅ | — |
| 91 | 2,6-dichlorophenyl | — | —CH₂— | pyrrolidino | phenyl | phenyl | —C(=O)OC₂H₅ | — |
| 92 | 2-chlorophenyl | — | —CH₂— | pyrrolidino | phenyl | phenyl | —C≡N | — |
| 93 | 2,6-dichlorophenyl | — | —CH₂— | pyrrolidino | phenyl | phenyl | —C≡N | — |

The following Examples are given for the purpose of illustrating the present invention:

EXAMPLE 1.

Ethyl 2,2-bis-(4-methoxyphenyl)-4-(1-pyrrolidino)-5-isobutoxyvalerate.

A solution of 27.1 g. (0.1 mole) isobutyl 2-(1-pyrrolidino)-3-isobutoxypropionate (cf. Federal Republic of Germany Patent Specification No. 28 02 864) in 100 ml. anhydrous tetrahydrofuran is added dropwise, while stirring, to an ice-cold suspension of 5.9 g. (0.15 ml) lithium aluminium hydride in 250 ml. anhydrous tetrahydrofuran in such a manner that the reaction temperature does not increase above 10° C. After completion of the addition, the reaction mixture is further stirred for 30 minutes at ambient temperature, subsequently mixed with 40 ml. of water and filtered with suction. The precipitate is washed three times with, in each case, 50 ml. tetrahydrofuran and the tetrahydrofuran then stripped off from the combined filtrates in a vacuum. The yellow oil remaining behind is then distilled in a vacuum. As main fraction, there is thus obtained 17.5 g. (87% of theory) 1-isobutoxy-2-(1-pyrrolidino)-3-hydroxypropane; b.p. 90° C./0.05 mm.Hg.

7.6 ml. (12.4 g.=0.1 mole) thionyl chloride in 50 ml. 1,2-dichloroethane are added dropwise to a solution, cooled to 0° C., of 16.1 g. (0.08 mole) 1-isobutoxy-2-(1-pyrrolidino)-3 -hydroxypropane in 100 ml. 1,2-dichloroethane. After completion of the addition, the reaction mixture is further stirred for 3 hours at ambient temperature, the excess thionyl chloride and the solvent are then stripped off on a rotary evaporator and the residue is taken up in 100 ml. methylene chloride. The methylene chloride solution is subsequently washed twice with, in each case, 50 ml. of a saturated aqueous solution of sodium hydrogen carbonate and once with water, dried over anhydrous sodium sulphate and evaporated in a vacuum. Vacuum distillation of the crude product gives 12.5 g. (71.2% of theory) 1-isobutoxy-2-(1-pyrrolidino)-3-chloropropane; b.p. 78° C./ 0.06 mm.Hg.

A solution of 3.3 g. (0.011 mole) ethyl 4,4'-dimethoxy-diphenylacetate (see A. Bistrzycki. I. Paulus and R. Perrin, Chem. Ber., 44, 2606) in 10 ml anhydrous toluene is added dropwise, with stirring, to a suspension of 0.27 g. (0.011 mole) sodium hydride in 50 ml. anhydrous toluene and 5 ml. anhydrous dimethylformamide and the reaction mixture thereafter stirred for 30 minutes at ambient temperature. Subsequently, a solution of 2 g. (0.009 mole) 1-isobutoxy-2-(1-pyrrolidino)-3-chloropropane in 10 ml. anhydrous toluene is added thereto and the reaction mixture heated for 2 hours at 100° C. After cooling, the toluene is stripped off in a vacuum, the residue is mixed with 10 ml. saturated aqueous ammonium chloride solution and the aqueous mixture extracted three times with, in each case, 20 ml. methylene chloride. After drying the combined organic phases over anhydrous sodium sulphate, the methylene chloride is stripped off on a rotary evaporator and the yellow oily residue purified by column chromatography to give 2.3 g. (53% of theory) ethyl 2,2-bis-(4-methoxyphenyl)-4-(1-pyrrolidino)-5-isobutoxyvalerate.

EXAMPLE 2.

2-Phenyl-2-(2-pyridyl)-4-(1-pyrrolidino)-5-isobutoxyvaleronitrile.

1.1 g. (5.7 mMole) 2-pyridylphenylacetonitrile (see Klosa, Arch. Pharm., 286/58, 435/1953) in 5 ml. anhydrous toluene is added, while stirring, to a suspension of 0.15 g. (6.2 mMole) 100% sodium hydride in 20 ml. anhydrous toluene and the reaction mixture is heated to 100° C. for 10 minutes. Subsequently, a solution of 1.1 g. (5 mMole) 1-isobutoxy-2-(1-pyrrolidino)-3-chloropropane in 5 ml. anhydrous toluene is added dropwise thereto and the reaction mixture heated under reflux for 2 hours. After cooling, the toluene is stripped off on a rotary evaporator, the residue is mixed with 10 ml. saturated aqueous ammonium chloride solution, the aqueous mixture is extracted three times with, in each case, 20 ml. methylene chloride and the combined organic phases are dried over anhydrous sodium sulphate. After stripping off the solvent and column chromatographic purification of the crude product, there is obtained 1.2 g. (64% of theory) 2-phenyl-2-(2-pyridyl)-4-(1-pyrrolidino)-5-isobutoxyvaleronitrile in the form of a colourless oil.

EXAMPLE 3.

Ethyl 2,2-diphenyl-4-(N,N-diethylamino)-5-isobutoxyvalerate.

217 ml. Epichlorohydrin are added dropwise, with vigorous stirring, to a mixture of 64 ml. isobutanol, 155 ml. concentrated aqueous sodium hydroxide solution and 2 g. tetrabutylammonium bromide in such a manner that the reaction temperature does not exceed 40° C. When the dropwise addition is complete, the reaction mixture is further stirred for 2 hours at ambient temperature and then mixed with 500 ml. of ice water. The organic phase is separated off, the aqueous phase is extracted twice with, in each case, 50 ml. methylene chloride and the combined organic phases are dried over anhydrous sodium sulphate. After stripping off the methylene chloride on a rotary evaporator, the residue is distilled in a vacuum. There are obtained 66 g. (72% of theory) isobutyl glycidyl ether; b.p. 66–70° C./40 mm.Hg.

A solution of 5.2 g. (0.04 mole) isobutyl glycidyl ether and 5.2 ml. (0.05 mole) diethylamine in 60 ml. anhydrous ethanol is boiled under reflux for 20 hours. Subsequently, the ethanol and excess diethylamine are stripped off on a rotary evaporator and the residue is purified by column chromatography. There are obtained 6.9 g. (85% of theory) 1-isobutoxy-2-hydroxy-3-(N,N-diethylamino)-propane in the form of a colourless oil.

1.2 ml. (16.4 mMole) thionyl chloride in 10 ml. 1,2-dichloroethane is added dropwise at ambient temperature to a solution of 3 g. (14.6 mMole) 1-isobutoxy-2-hydroxy-3-(N,N-diethylamino)-propane in 30 ml. 1,2-dichloroethane. Subsequently, the reaction mixture is heated under reflux for 2 hours, cooled, extracted twice with, in each case, 50 ml. of a saturated aqueous solution of sodium hydrogen carbonate and the organic phase then dried over anhydrous sodium sulphate. After stripping off the solvent, the residue is chromatographed on silica gel. There are obtained 2 g. (62.5% of theory) 1-isobutoxy-2-chloro-3-(N,N-diethylamino)-propane in the form of a yellow oil.

2 g. (8.3 mMole) Ethyl diphenylacetate in 10 ml. anhydrous toluene are added at ambient temperature to a stirred suspension of 200 mg. (8.3 mMole) sodium hydride in 30 ml. anhydrous toluene and 1 ml. dimethylformamide and the reaction mixture subsequently heated for 20 minutes to 80° C. Thereafter, a solution of 1.6 g. (7.2 mMole) 1-isobutoxy-2-chloro-3-(N,N-diethylamino)-propane in 5 ml. anhydrous toluene is added dropwise thereto at 80° C. and the reaction mixture heated under reflux for 2 hours. After cooling, the reaction mixture is mixed with 20 ml. of a saturated aqueous solution of ammonium chloride and the organic phase is separated off and dried over anhydrous sodium sulphate. After stripping off the solvent, the crude product is purified by column chromatography. There is obtained 1.4 g. (46% of theory) ethyl 2,2-diphenyl-4-(N,N-diethylamino)-5-isobutoxyvalerate in the form of a colourless oil.

EXAMPLE 4.

Ethyl 2,2-diphenyl-4-(1-pyrrolidino)-5-benzyloxyvalerate.

21.7 ml. (277 mMole) epichlorohydrin are added at 15 to 20° C., with vigorous stirring and in the course of 20 minutes, to a mixture of 7.6 g. (70.5 mMole) benzyl alcohol and 0.2 g. tetrabutylammonium bromide in 16 ml. concentrated aqueous sodium hydroxide solution. The reaction mixture is subsequently stirred for 3 hours at 40° C. After cooling, the reaction mixture is mixed with 50 ml. iced water, the organic phase is separated off and the aqueous phase is extracted twice with, in each case, 20 ml. methylene chloride. After drying the combined organic phases over anhydrous sodium sulphate and stripping off the solvent on a rotary evaporator, there are obtained 11.5 g. crude benzyl glycidyl ether.

11.5 g. of the crude benzyl glycidyl ether are dissolved in 300 ml. anhydrous ethanol and mixed with 25 ml. pyrrolidine. Subsequently, the reaction solution is heated under reflux for 3 hours, the solvent and the excess pyrrolidine are then stripped off on a rotary evaporator, the residue is mixed with 100 ml. water, the aqueous solution is extracted three times with, in each case, 50 ml. methylene chloride and the combined organic phases are dried over anhydrous sodium sulphate. At 0.05 mm.Hg and 114–118° C., there are obtained 15.2 g. (92% of theory) 1-benzyloxy-2-hydroxy-3-(1-pyrrolidino)-propane in the form of a colourless liquid.

1.2 ml. (16.4 mMole) thionyl chloride in 10 ml. 1,2-dichloroethane is added dropwise at ambient temperature to a solution of 3.4 g. (14.5 mMole) 1-benzyloxy-2-hydroxy-3-(1-pyrrolidino)-propane in 30 ml. 1,2-dichloroethane. The reaction solution is subsequently heated under reflux for 2 hours, then cooled, extracted twice with, in each case, 50 ml. saturated aqueous sodium hydrogen carbonate solution and the organic phase dried over anhydrous sodium sulphate. After stripping off the solvent, the residue is chromatographed. There are obtained 2.5 g. (68% of theory) 1-benzyloxy-2-chloro-3-(1-pyrrolidino)-propane.

2 g. (8.3 mMole) Ethyl diphenylacetate in 10 ml. anhydrous toluene are added at ambient temperature to a stirred suspension of 200 mg. (8.3 mMole) sodium hydride in 30 ml. anhydrous toluene and 1 ml. dimethylformamide and the mixture is subsequently heated to 80° C. for 20 minutes. Thereafter, a solution of 2 g. (7.9 mMole) 1-benzyloxy-2-chloro-3-(1-pyrrolidino)-propane in 5 ml. anhydrous toluene is added dropwise thereto at 80° C. and then heated under reflux for 2 hours. After cooling, the reaction mixture is mixed with 20 ml. of a saturated aqueous solution of ammonium chloride and the organic phase is separated off and dried over anhydrous sodium sulphate. After stripping off the solvent, the crude product is purified by column chromatography. There is obtained 1.7 g. (47% of theory) ethyl 2,2-diphenyl-4-(1-pyrrolidino)-5-benzyloxyvalerate in the form of a colourless oil.

EXAMPLE 5.

Ethyl 2,2-diphenyl-4-(1-pyrrolidino)-5-(2-picolyloxy)valerate.

190 ml. (2.4 mole) Epichlorohydrin are added dropwise with vigorous stirring at 15–20° C. to a mixture of 50 ml. (0.52 mole) pyridine-2-carbinol and 8 g. (0.025 mole) tetrabutyl-ammonium bromide in 200 ml. concentrated aqueous sodium hydroxide solution. Subsequently, the reaction mixture is stirred overnight at ambient temperature and then mixed with 500 ml. iced water. The organic phase is separated off, the aqueous phase is extracted three times with diethyl ether and the combined organic phases are dried over anhydrous sodium sulphate. After stripping off the solvent and excess epichlorohydrin on a rotary evaporator, there are obtained 57.8 g. crude 2-picolyl glycidyl ether.

57.8 g. of crude 2-picolyl glycidyl ether are dissolved in 100 ml. ethanol and mixed with 58 ml. pyrrolidine. The reaction mixture is subsequently heated for 1 hour at 50° C., the solvent and excess pyrrolidine are then stripped off and the residue is distilled in a vacuum. There are obtained 57 g. (69% of theory) 1-(2-picolyloxy)-2-hydroxy-3-(1-pyrrolidino)-propane; b.p. 133° C./0.01 mm.Hg.

18 ml. Thionyl chloride in 100 ml. 1,2-dichloroethane are added dropwise at ambient temperature to a solution of 48 g. (0.2 mole) 1-(2- picolyloxy)-2-hydroxy-3-(1-pyrrolidino)-propane in 600 ml. 1,2-dichloroethane. The reaction mixture is subsequently heated under reflux for 4 hours, then allowed to cool and poured on to 500 ml. iced water. Thereafter, the organic phase is separated off and extracted twice with, in each case, 50 ml. 1N hydrochloric acid. The combined aqueous phases are rendered weakly alkaline with 1N aqueous sodium hydroxide solution (pH 8–9). The alkaline solution is now extracted three times with, in each case, 100 ml. methylene chloride, the combined organic phases are dried over anhydrous sodium sulphate and the solvent subsequently stripped off on a rotary evaporator. There are obtained 50 g. (96.6% of theory) crude 1-(2-picolyloxy)-2-chloro-3-(1-pyrrolidino)-propane.

10 g. (0.04 mole) 1-(2-picolyloxy)-2-chloro-3-(1-pyrrolidino)-propane and 12 g. (0.05 mole) ethyl diphenylacetate are dissolved in 100 ml. anhydrous dimethylformamide, the solution is mixed with 1.2 g. (0.05 mole) sodium hydride and the reaction mixture is subsequently heated to 80° C. for 1 hour. Thereafter, the cooled reaction solution is mixed with 200 ml. saturated aqueous ammonium chloride solution and extracted three times with, in each case, 50 ml. methylene chloride. After drying the combined organic phases over anhydrous sodium sulphate and stripping off the solvent, the residue is chromatographed. There are obtained 9.2 g. (50.3% of theory) of the title compound in the form of a bright yellow oil which crystallises upon trituration; m.p. 68° C.

The following compounds are prepared in an analogous manner (compounds 14, 17 and 20 in the following table are identified in Table 1 of the following description of the in vitro test results identified as 5/14, 5/17 and 5/20):

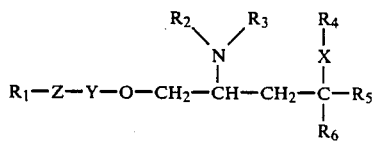

| Ex. No. | R₁ | Z | Y | R₂, R₃ | R₄ | R₅ | R₆ | X |
|---|---|---|---|---|---|---|---|---|
| 1 | (CH₃)₂—CHCH₂— | — | — | ⌑ | ⌬ | ⌬ | —C(=O)OC₂H₅ | —CH₂— |
| 2 | (CH₃)₂—CHCH₂— | — | — | ⌑ | ⌬ | —H | —C≡N | — |

4,999,361

-continued

| # | | | | ring1 | ring2 | ring3 | group | |
|---|---|---|---|---|---|---|---|---|
| 3 | (CH₃)₂—CHCH₂— | — | — | cyclopentyl | phenyl | —H | —C(=O)OC₂H₅ | — |
| 4 | (CH₃)₂—CHCH₂— | — | — | cyclopentyl | phenyl | —C(=O)OC₂H₅ | —C(=O)OC₂H₅ | — |
| 5 | (CH₃)₂—CHCH₂— | — | — | cyclopentyl | phenyl | —C≡N | —C(=O)OC₂H₅ | — |
| 6 | (CH₃)₂—CHCH₂— | — | — | cyclopentyl | phenyl | phenyl | —H | — |
| 7 | (CH₃)₂—CHCH₂— | — | — | cyclopentyl | phenyl | phenyl | —C(=O)OC₂H₅ | — |
| 8 | (CH₃)₂—CHCH₂— | — | — | cyclopentyl | phenyl | phenyl | —C≡N | — |
| 9 | (CH₃)₂—CHCH₂— | — | — | cyclopentyl | phenyl | phenyl | —C(=O)OH | — |
| 10 | (CH₃)₂—CHCH₂— | — | — | cyclohexyl | phenyl | phenyl | —C(=O)OC₂H₅ | — |
| 11 | (CH₃)₂—CHCH₂— | — | — | tetrahydropyranyl (O) | phenyl | phenyl | —C(=O)OC₂H₅ | — |
| 12 | (CH₃)₂—CHCH₂— | — | — | cyclopentyl | 4-OCH₃-phenyl | 4-OCH₃-phenyl | —C≡N | — |
| 13 | (CH₃)₂—CHCH₂— | — | — | cyclopentyl | 2-thienyl | 2-thienyl | —C(=O)OC₂H₅ | — |

-continued
| | | | | | | | |
|---|---|---|---|---|---|---|---|
| 14 | CH₂=C(CH₃)—CH₂— | — | — |  |  |  | —C(=O)OC₂H₅ | — |
| 15 | CH₂=C(CH₃)—CH₂— | — | — |  |  |  | —C≡N | — |
| 16 | (CH₃)₂C=CH—CH₂— | — | — |  |  |  | —C(=O)OC₂H₅ | —CH₂— |
| 17 | (CH₃)₂C=CH—CH₂— | — | — |  |  |  | —C(=O)OC₂H₅ | — |
| 18 | CH₂=C(CH₃)—(CH₂)₂— | — | — |  |  |  | —C(=O)OC₂H₅ | —CH₂— |
| 19 | CH₂=C(CH₃)—(CH₂)₂— | — | — |  |  |  | —C(=O)OC₂H₅ | — |
| 20 | CH₂=CH—C(CH₃)₂— | — | — |  |  |  | —C(=O)OC₂H₅ | — |
| 21 | CH₂=C(CH₃)—CH₂ | — | — |  |  |  | —C(=O)OC₂H₅ | —CH₂— |
| 22 | 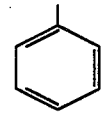 | — | — |  |  |  | —C(=O)OC₂H₅ | — |
| 23 | 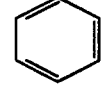 | — | — |  |  |  | —C≡N | — |
| 24 | 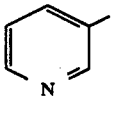 | — | —CH₂— |  |  |  | —C(=O)OC₂H₅ | — |

-continued
| | | | | | | | |
|---|---|---|---|---|---|---|---|
| 25 | 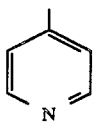 | — | —CH$_2$— |  | 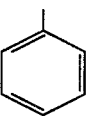 | 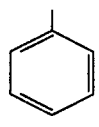 | 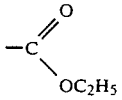 — |
| 26 | 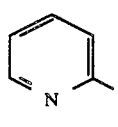 | — | —CH$_2$— |  | 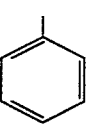 | 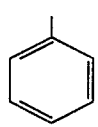 | 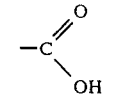 — |
| 27 | 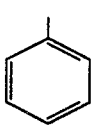 | — | —CH$_2$— |  | 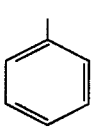 | 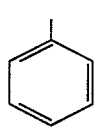 | 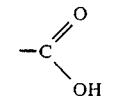 — |
| 28 | 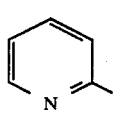 | — | — |  | 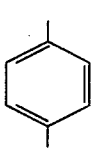 | 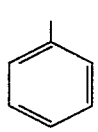 | 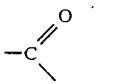 —CH$_2$— |
| 29 | 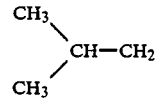 | — | — |  | 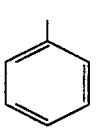 | 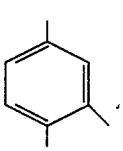 | 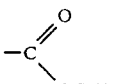 —CH$_2$— |
| 30 | 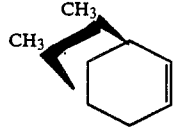 | — | —CH$_2$— |  | 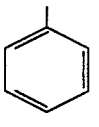 | 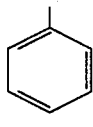 | 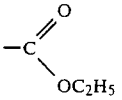 — |
| 31 | 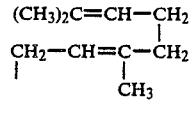 | — | — |  | 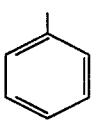 | 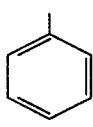 | 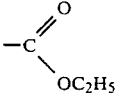 — |
| 32 | 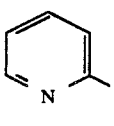 | — | —CH$_2$— |  | 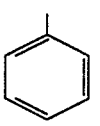 | 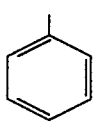 | —CH$_2$OH — |
| 33 | 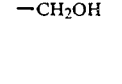 | — | —CH$_2$— | 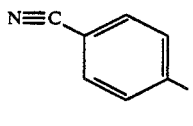 |  | 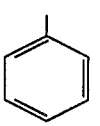 | 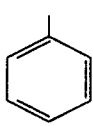 — |
| 34 | 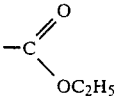 | — | —CH$_2$— | 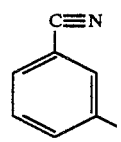 |  | 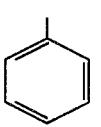 | 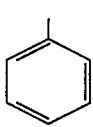 — |
| 35 | 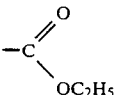 | — | —CH$_2$— | 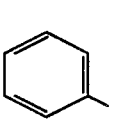 |  | 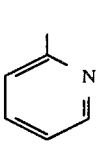 | —C≡N — |

| 36 | 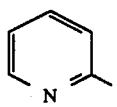 | — | —CH$_2$— |  | 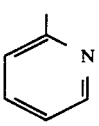 | 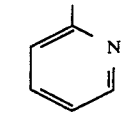 | —C≡N | — |

| | | | | | | | | |
|---|---|---|---|---|---|---|---|---|
| Ex. 1: | oil, m/e 437 | | | Ex. 13: | oil, m/e 435 | | Ex. 25: | oil, m/e 458 |
| Ex. 2: | oil, m/e 300 | | | Ex. 14: | oil, m/e 421 | | Ex. 26: | m.p. 180° C. |
| Ex. 3: | oil, m/e 347 | | | Ex. 15: | oil, m/e 374 | | Ex. 27: | m.p. 182° C. |
| Ex. 4: | oil, m/e 419 | | | Ex. 16: | oil, m/e 449 | | Ex. 28: | oil, m/e 502 |
| Ex. 5: | oil, m/e 372 | | | Ex. 17: | oil, m/e 435 | | Ex. 29: | oil, m/e 481 |
| Ex. 6: | oxalate, m.p. 105° C., ethyl acetate | | | Ex. 18: | oil, m/e 449 | | Ex. 30: | oil, m/e 581 |
| Ex. 7: | oil, m/e 423 | | | Ex. 19: | oil, m/e 435 | | Ex. 31: | oil, m/e 503 |
| Ex. 8: | solid, m.p. °C., heptane | | | Ex. 20: | oil, m/e 435 | | Ex. 32: | m.p. 63–65° C. |
| Ex. 9: | solid, m.p. 198° C., ethyl acetate | | | Ex. 21: | oil, m/e 435 | | Ex. 33: | oil, m/e 482 |
| Ex. 10: | oil, m/e 437 | | | Ex. 22: | oil, m/e 443 | | Ex. 34: | oil, m/e 482 |
| Ex. 11: | oil, m/e 439 | | | Ex. 23: | oil, m/e 396 | | Ex. 35: | oil, m/e 412 |
| Ex. 12: | oil, m/e 436 | | | Ex. 24: | oil, m/e 458 | | Ex. 36: | oil, m/e 413 |

In Vitro Test Results

Rat aorta segments were suspended in an organ bath (10 ml) and connected to a force pickup, and stretched to 15 mN. The Krebs-Henseleit solution in the organ bath had the following composition:

NaCl—118 mM; KCl—4.7 mM; MgSO$_4$=1.2 mM; CaCl$_2$=2.5 mM; KH$_2$PO$_4$=1.2 mM; NaHCO$_3$=25 mM; glucose=11 mM.

The aorta segments were left in the bath for 45 minutes, to reach equilibrium, and then a stock solution of KCl was added to the organ bath to increase the KCl concentration of the nutrient solution in the organ bath to 40 mM. After the aorta segments had been exposed for 30 minutes to the increased potassium concentration, the test substances were added at an identical concentration ($10^{-6}$ mol/liter) to the bath solution. The test substances produced a relaxation effect which varied with the different test substances, and is reported in Table 1 below as a percent of the pre-contraction, determined 25 minutes after the test substance addition to the bath solution. The percent relaxation reported is a measure of the Ca++ antagonistic effect of the respective test substances. The higher the percent relaxation value reported in the right-hand column of Table 1, the more active the substance.

TABLE 1

% relaxation following pre-contraction with 40 mM K+ions.
Incubation time: 25 minutes
Concentration of the test compound: $10^{-6}$ M/liter
Number of tested preparations per substance: n=4

| Compound (example) | Relaxation (%) |
|---|---|
| Bepridil | 51 |
| 4 | 74 |
| 5/17 | 80 |
| 5/14 | 80 |
| BV 70 | 76 |
| BV 71 | 93 |
| BV 72 | 82 |
| 5 | 98 |
| 5/20 | 74 |
| BV 66 | 76 |
| BV 2 | 83 |

Bepridil = β-[2-Methylpropoxy)methyl]-N-phenyl-N-(phenylmethyl)-1-pyrrolidineethanamine. (Comparison compound of U.S. Pat. No. 3,962,238)

Bepridil = β-[2-Methylpropoxy)methyl]-N-phenyl-N-(phenylmethyl)-1-pyrrolidineethanamine. (Comparison compound of U.S. Pat. No. 3,962,238)

As will be appreciated from Table 1, the compounds of the present invention are cardiovascular agents exhibiting antianginal and antiarrhythemic properties.

What is claimed is:

1. A compound of the formula:

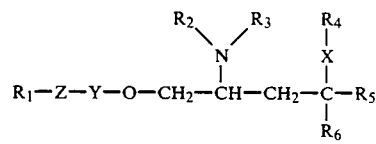

wherein R$_1$ is isobutyl, methallyl, isopentenyl, furyl, thienyl, pyridyl, phenyl or phenyl or phenyl substituted by methyl, methoxy or halogen; R$_2$ and R$_3$, together with the nitrogen atom to which they are attached, form a pyrrolidine ring; R$_4$ is phenyl or phenyl substituted by methoxy or halogen; R$_5$ is pyridyl, phenyl or phenyl substituted by methoxy, methylenedioxy or halogen; R$_6$ is hydrogen, cyano, methoxycarbonyl, ethoxycarbonyl or hydroxymethyl; X is a valency bond; Y is a valency bond, methylene or ethylene; and Z is a valency bond; or a pharmacologically acceptable salt or optical isomer thereof.

2. A compound according to claim 1, wherein R$_5$ is phenyl or phenyl substituted by methylenedioxy, methoxy or halogen.

3. A compound according to claim 1, wherein R$_6$ is hydrogen, cyano, methoxycarbonyl, ethoxycarbonyl, or hydroxy methyl.

4. A compound according to claim 1, which is ethyl 2,2-diphenyl-4-(1-pyrrolidino)-5-benzyloxyvalerate.

5. A compound according to claim 1, wherein R$_1$ is CH$_3$(CH$_3$)C=CH—CH$_2$—; R$_2$ and R$_3$, together with the nitrogen atom to which they are attached, form a pyrrolidine ring; R$_4$ and R$_5$ are each phenyl; R$_6$ is ethoxycarbonyl, and X, Y and Z are each a valency bond.

6. A compound according to claim 1, wherein R$_1$ is CH$_2$=C(CH$_3$)CH$_2$—; R$_2$ and R$_3$, together with the nitrogen atom to which they are attached, form a pyrrolidine ring; R$_4$ and R$_5$ are each phenyl; R$_6$ is ethoxycarbonyl, and X, Y and Z are each a valency bond.

7. A compound according to claim 1, wherein R$_1$ is phenyl; R$_2$ and R$_3$, together with the nitrogen atom to which they are attached, form a pyrrolidine ring; R$_4$ and 8. A compound according to claim 1, wherein $R_1$ is furyl; $R_2$ and $R_3$, together with the nitrogen atom to which they are attached, form a pyrrolidine ring; $R_4$ and $R_5$ are each phenyl; $R_6$ is ethoxycarbonyl; X is a valency bond; Y is —$CH_2$— and Z is a valency bond.

9. A compound according to claim 1, wherein $R_1$ is thienyl; $R_2$ and $R_3$, together with the nitrogen atom to which they are attached, form a pyrrolidine ring; $R_4$ and $R_5$ are each phenyl; $R_6$ is ethoxycarbonyl; X is a valency bond; Y is —$CH_2$— and Z is a valency bond.

10. A compound according to claim 1, wherein $R_1$ is 2-pyridyl; $R_2$ and $R_3$, together with the nitrogen atom to which they are attached form a pyrrolidine ring; $R_4$ and $R_5$ are each phenyl; $R_6$ is ethoxycarbonyl; X is a valency bond; Y is —$CH_2$— and Z is a valency bond.

11. A compound according to claim 1, wherein $R_1$ is $CH_2$=$CHC(CH_3)_2$—; $R_2$ and $R_3$, together with the nitrogen atom to which they are attached, form a pyrrolidine ring; $R_4$ and $R_5$ are each phenyl; $R_6$ is ethoxycarbonyl, and X, Y and Z are each a valency bond.

12. A compound according to claim 1, wherein $R_1$ is phenyl; $R_2$ and $R_3$, together with the nitrogen atom to which they are attached, form a pyrrolidine ring; $R_4$ and $R_5$ are each phenyl; $R_6$ is methoxycarbonyl, X is a valency bond, Y is —$CH_2$— and Z is a valency bond.

13. Ethyl 2,2-dipheny-4-(1-pyrrolidino)-5-(2-picolyloxy)-valerate, a compound according to claim 10.

14. A pharmaceutical composition suitable for treatment of heart and circulatory diseases comprising a therapeutically effective amount of a compound of claim 1 and a pharmaceutically acceptable carrier.

15. A method of producing a blood vessel relaxing effect in a patient in need of such effect, comprising administering to said patient a blood vessel relaxing amount of a compound of claim 1.

16. The method of claim 15, wherein said blood vessel relaxing amount is 50 to 1000 mg per dose administered 1 to 3 times daily.

* * * * *